US005695471A

United States Patent [19]
Wampler

[11] Patent Number: 5,695,471
[45] Date of Patent: Dec. 9, 1997

[54] SEALLESS ROTARY BLOOD PUMP WITH PASSIVE MAGNETIC RADIAL BEARINGS AND BLOOD IMMERSED AXIAL BEARINGS

[75] Inventor: Richard K. Wampler, Granite Bay, Calif.

[73] Assignee: Kriton Medical, Inc., Del.

[21] Appl. No.: 603,536

[22] Filed: Feb. 20, 1996

[51] Int. Cl.$^6$ .................................................. A61M 37/00
[52] U.S. Cl. .................. 604/131; 417/423.1; 417/423.7; 604/151
[58] Field of Search .................. 623/3; 417/321, 417/423.1, 423.7, 423.12, 203, 206; 604/131, 151

[56] References Cited

U.S. PATENT DOCUMENTS

| | | |
|---|---|---|
| 2,725,266 | 11/1955 | Mendelsohn . |
| 3,487,784 | 1/1970 | Rafferty et al. . |
| 3,493,274 | 2/1970 | Emslie et al. . |
| 3,957,389 | 5/1976 | Rafferty et al. . |
| 4,057,369 | 11/1977 | Isenberg et al. . |
| 4,072,370 | 2/1978 | Wasson . |
| 4,135,253 | 1/1979 | Reich et al. . |
| 4,253,798 | 3/1981 | Sugiura . |
| 4,382,245 | 5/1983 | Harrigan . |
| 4,507,048 | 3/1985 | Belenger et al. . |
| 4,625,712 | 12/1986 | Wampler . |
| 4,688,998 | 8/1987 | Olsen et al. . |
| 4,704,121 | 11/1987 | Moise . |
| 4,745,345 | 5/1988 | Petersen . |
| 4,763,032 | 8/1988 | Bramm et al. . |
| 4,779,614 | 10/1988 | Moise . |
| 4,789,251 | 12/1988 | McPherson et al. . |
| 4,806,080 | 2/1989 | Mizobuchi et al. . |
| 4,846,152 | 7/1989 | Wampler et al. . |
| 4,908,012 | 3/1990 | Moise et al. . |
| 4,994,078 | 2/1991 | Jarvik . |
| 5,017,103 | 5/1991 | Dahl . |
| 5,049,134 | 9/1991 | Golding et al. . |

(List continued on next page.)

OTHER PUBLICATIONS

Tanaka et al., "A New Seal–Less Centrifugal Blood Pump", Japan Journal of Artifical Organs, 14 (3), pp. 1126–1129, (1985).

Nishida et al., "Development of the Terumo Capiox Centrifugal Pump and Its Clinical Application to Open Heart Surgery: A Comparative Study with the Roller Pump", pp. 24–28, (1992).

Kijima et al., "A Straight Path Centrifugal Blood Pump Concept in the Capiox Centrifugal Pump", pp. 32–37, (1993).

(List continued on next page.)

*Primary Examiner*—Sam Rimell
*Attorney, Agent, or Firm*—Gerstman, Ellis & McMillin, Ltd.

[57] ABSTRACT

An implantable rotary blood pump without a shaft seal. The pump includes a rotary element, having a pump impeller on one end. The impeller is specially designed with large, thick blades and tall, narrow blood channels, to minimize hemolysis. The rotary element and the impeller are maintained in radial alignment by respective, passive magnetic bearings. Axial restraint of the rotary element is provided by blood immersed thrust bearings, spaced a slight distance from either end of the rotor. Drive for the rotary element is provided by a structurally integrated, brushless electric motor. A plurality of permanent magnets is arranged in circular fashion within the impeller, constituting a rotor for the motor. The motor's stator includes circular windings of conductive wire, located within the pump housing and concentric with the rotor. With the stator energized, electromagnetic forces between the stator and the motor rotor cause the rotary element and the impeller to rotate. During operation, the rotary element shuttles back and forth along its axis between the thrust surfaces in response to heart pulsations. This bi-stable operation of the pump, allows fresh blood to flush through the thrust bearings in continuous fashion, minimizing the likelihood of thrombosis developing from operation of the pumps.

44 Claims, 4 Drawing Sheets

U.S. PATENT DOCUMENTS

| | | |
|---|---|---|
| 5,055,005 | 10/1991 | Kletschka . |
| 5,078,741 | 1/1992 | Bramm et al. . |
| 5,106,263 | 4/1992 | Irie . |
| 5,112,202 | 5/1992 | Oshima et al. . |
| 5,149,253 | 9/1992 | Miyamoto et al. . |
| 5,160,246 | 11/1992 | Horiuchi . |
| 5,182,533 | 1/1993 | Ritts . |
| 5,195,877 | 3/1993 | Kletschka . |
| 5,201,642 | 4/1993 | Hinckley . |
| 5,211,546 | 5/1993 | Isaacson et al. . |
| 5,290,236 | 3/1994 | Mathewson . |
| 5,302,091 | 4/1994 | Horiuchi . |
| 5,316,440 | 5/1994 | Kijima et al. . |
| 5,342,825 | 8/1994 | Iannello et al. . |
| 5,385,581 | 1/1995 | Bramm et al. . |
| 5,399,074 | 3/1995 | Nose et al. . |
| 5,441,535 | 8/1995 | Takahashi et al. . |
| 5,443,503 | 8/1995 | Yamane . |
| 5,470,208 | 11/1995 | Kletschka . |
| 5,507,629 | 4/1996 | Jarvik . |
| 5,527,159 | 6/1996 | Bozeman, Jr. et al. . |
| 5,575,630 | 11/1996 | Nakazawa et al. . |

OTHER PUBLICATIONS

Yamane et al. "Fundamental Characteristics of Magnetically Suspended Centrifugal Blood Pump", pp. 130–131 (1994).

Kijima et al., "The Margin of Safety in the Use of a Straight Path Centrifugal Blood Pump", *Artifical Organs*, 18(9), pp. 680–686, (1994).

"Implantable Artifical Cardiac Blood Pump Prototype Developed", Medical Equipment Journal of Japan, (May 1994).

Yamane et al., "Design of a Centrifugal Blood Pump with Magnetic Suspension", 1 page, Abstract, (Sep. 1994).

Yamane et al., "Design of a Centrifugal Blood Pump with Magnetic Suspension", *Artificial Organs*, 19(7) pp. 625–630, (1995).

Akamatsu et al., "Recent Studies of the Centrifugal Blood Pump with a Magnetically Suspended Impeller", *Artificial Organs*, 19(7), pp. 631–634, (1995).

Yamane "Peformance Improvements of a Centrifugal Blood Pump with Mono–Pivot Magnetic–Suspension", pp. 538–539, (1996).

SEALLESS ROTARY BLOOD PUMP WITH PASSIVE MAGNETIC RADIAL BEARINGS AND BLOOD IMMERSED AXIAL BEARINGS

FIELD OF THE INVENTION

The invention relates generally to the field of blood pumps. More specifically, the invention pertains to continuous flow pumps of rotary design, suitable for permanent implantation in humans, for use as chronic ventricular assist devices.

BACKGROUND OF THE INVENTION

Thousands of heart patients who suffer from severe left ventricular heart failure could benefit from cardiac transplantation. However, owing to a shortage of donor hearts, most of these patients face a foreshortened life span characterized by frequent hospitalizations, severe physical disability, and death from congestive failure or cardiogenic shock. If a left ventricular assist device ("LVAD") were available for chronic use, many of these patients could be returned to prolonged and productive lives.

Prior art LVADs, now in clinical trials, provide a cyclic or pulsating delivery of blood, designed to emulate the natural pulsatile blood flow through the heart. This design approach has resulted in a variety of anatomic and engineering problems. Cyclic delivery systems tend to be physically large, making implantation difficult or impossible for some patients. Cyclic delivery systems also employ artificial valves, having special material, longevity, and performance requirements. All of these characteristics make cyclic blood pumping devices both complex and expensive.

It is apparent that if the requirement of pulsatile blood flow is eliminated, the LVAD could be much smaller, simpler, and less expensive. Rotary pumps, whether of centrifugal or axial flow design, provide substantially continuous liquid flow, and potentially enjoy a number of the listed advantages over cyclic delivery systems. However, the prior art has not developed a durable rotary blood pump, owing to unique problems with the rotary pump's driveshaft seal. In a blood environment, such driveshaft seals have a short life, and contribute to a premature failure of the pump. Prior art driveshaft seals may also cause embolisms, resulting in a stroke or even death for the patient.

Accordingly, it is an object of the present invention to provide an improved rotary blood pump, by eliminating the necessity for a driveshaft seal;

It is a further object of the present invention to provide a compact, rotary blood pump using passive, magnetic radial bearings to maintain an impeller and its support shaft for rotation about an axis;

It is yet a further object of the present invention to provide a rotary blood pump having bi-stable operation, in which the impeller and the support shaft shuttle as a unit, between two predetermined axial positions;

It is another object of the present invention to provide blood immersed axial thrust bearings which are regularly washed by fresh blood flow to prevent thrombosis from occurring;

It is yet another object of the present invention to provide a unique thick bladed pump impeller, which houses both motor magnets and radial bearing magnets, and includes narrow, deep, blood flow passages;

It is yet another object of the present invention to provide a pump impeller which is effective pumping viscous liquids, such as blood, at low flow rates, and which minimizes hemolysis of the blood by using only a few pump impeller blades.

SUMMARY OF THE INVENTION

In accordance with the present invention, a rotary blood pump includes a housing and a pump rotor. A centrifugal pump impeller is attached to an impeller support shaft, or spindle, to form the pump rotor. The pump housing includes an elongated inlet tube surrounding the shaft, and a scroll-shaped casing, or volute, with a discharge outlet, enclosing the impeller.

The shaft and the impeller are specially suspended within the housing. Radial magnetic bearings of passive design, maintain the support shaft and the impeller about a rotational axis. The magnetic bearing which levitates the shaft includes a plurality of permanent ring magnets and pole pieces arranged along surrounding portions of the inlet tube, and a plurality of permanent disc magnets and pole pieces within the shaft itself. Radially adjacent pairs of these magnets are of like polarity. One part of the magnetic bearing, which maintains the impeller about a rotational axis, includes a plurality of permanent rod or arcuate magnets disposed in spaced, circular relation around blade sectors of the impeller; another part of the bearing includes a pair of permanent ring magnets outside the casing, on either side of the impeller. Adjacent portions of the rod and ring magnets are of opposite polarity.

The shaft and impeller are axially restrained by a magnetic and hydrodynamic forces in combination with mechanical thrust bearings, or touchdowns. The magnets of the magnetic bearing in the inlet tube and shaft may be arranged in slightly offset axial relation, to produce a translational loading force, or bias, along the longitudinal axis of the rotor. This bias substantially counteracts the axial force resulting from the hydraulic thrust of the rotating impeller. However, the hydraulic thrust will vary as a function of the cardiac cycle and additional restraints are desirable to ensure that pump operation is stable and controlled. For this purpose, a pair of blood immersed thrust bearings is provided. These thrust bearings may be located at either end of the rotor, although other arrangements are feasible.

One thrust bearing is included at the upstream end of the support shaft, and the other thrust bearing is located on the bottom, or downstream side of the impeller. A spider within the inlet tube includes a touchdown, or thrust surface, against which the end of the shaft periodically touches. Another touchdown is provided on an inner surface of the casing base, adjacent a downstream terminus of the impeller. A predetermined amount of spacing is included between the two touchdowns, so as to allow the shaft/impeller assembly axially to shuttle back and forth, in response to the user's cardiac cycle. This shuttling motion will produce a pumping action, frequently exchanging blood in the touchdown area with fresh blood from the circulation. This pumping action minimizes the likelihood of blood thrombosis in the thrust region, by maintaining the blood at an acceptable temperature and by shortening its residence time in the thrust bearing gap.

The impeller is of unique configuration and characteristics, owing to the special requirements of the present application. Contrary to conventional centrifugal pump design, the present invention uses relatively few impeller blades, generally resembling pie-shaped sectors. Moreover, the blades are made quite thick in an axial direction, having deep and narrow, arcuate channels between adjacent blades for the passage of blood through the impeller. The substantial height of the blades provides a relatively large blade working surface, ensuring efficient pump operation. These structural features decrease hemolysis of the blood, while maintaining useful efficiency in a pump using so few impeller blades.

Sealed, hollow chambers are provided within the thick impeller blades to reduce the density of the impeller. These chambers reduce gravity induced loads on the thrust bearings, which in turn reduces the likelihood of thrombosis of the blood used to lubricate the bearings.

The thick impeller blades are also used advantageously to house magnets used in the pump drive system. Torque drive is imparted to the impeller by magnetic interaction between arcuate, permanent magnetic segments imbedded within each impeller blade sector, and a circular electromagnetic stator, affixed to the casing. Back-EMF sensing is used to commutate the brushless motor stator, providing attractive and repulsive forces upon the magnetic segments. A control unit and a portable power supply, worn on the user, power the pump drive system. The control unit allows the speed and drive cycle of the motor either to be programmed or interactively determined by the user's physical activity or condition.

DETAILED DESCRIPTION OF THE PREFERRED EMBODIMENT

Turning now to the drawings, a sealless rotary blood pump 11 includes a housing 12, having an elongated inlet tube 13 and a scroll-shaped impeller casing or volute 14. A discharge tube 16 extends through the housing to communicate with the interior periphery of casing 14. Tube 16 has a tangential orientation with respect to a radius of the casing, for effectively channeling the blood output from the pump.

A pump rotor 17 is located within housing 12, and includes an elongated, right-circular cylindrical support shaft or spindle 18, attached to a disc-shaped impeller 19. Rotor 17 is mounted for rotation about a longitudinal axis which extends both through shaft 18 and impeller 19. It should be noted that the preferred embodiment disclosed herein includes an impeller and a casing of centrifugal design. However, many of the structural features and aspects of operation of the present invention may also be adapted advantageously to rotary blood pumps of axial flow design.

The pump 11 of the present invention includes a forward magnetic bearing 21 and a rearward magnetic bearing 22 to levitate rotor 17 and maintain it in proper radial alignment with respect to its longitudinal axis. A radial magnetic bearing construction is shown in U.S. Pat. No. 4,072,370, issued to Wasson. The '370 Patent is hereby expressly incorporated by reference. The forward magnetic bearing 21 herein may be constructed entirely in accordance with the teachings of the '370 Patent. However, several simplifications and improvements to the construction shown in the '370 Patent are disclosed herein. For example, it has been determined that the radially polarized ring magnets (numerals 44 and 46) of the '370 device, are not necessary for successful practice of the invention herein. In addition, as will be explained below, the axially magnetized ring magnets (numeral 22) of the '370 device may advantageously be replaced with axially magnetized disc magnets for purposes of the present invention.

Figure 7:
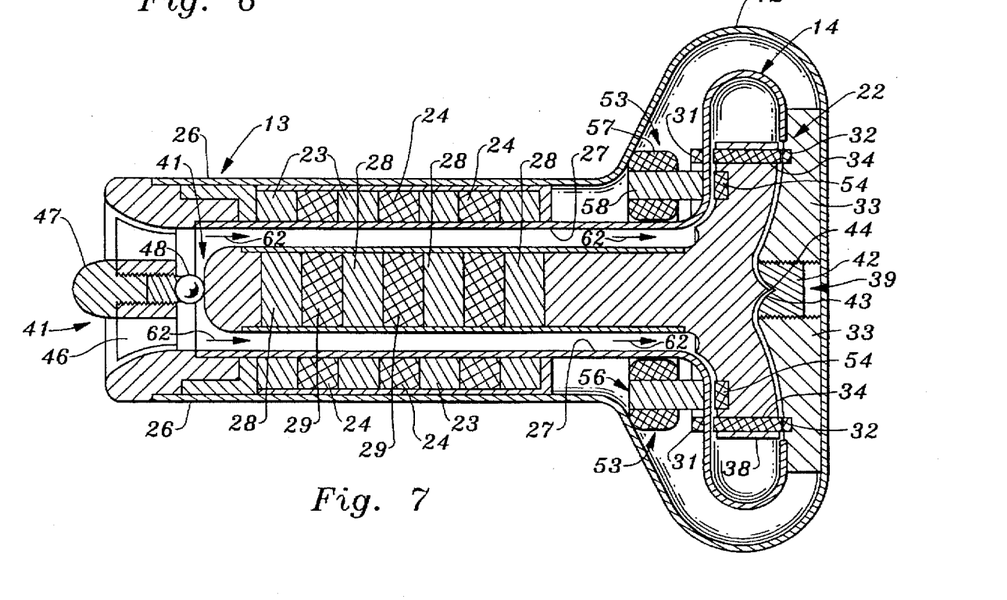
FIG. 7 is a longitudinal, cross-sectional view of the pump, taken along the line 7—7, shown in FIG. 1; and, FIG. 8 is a longitudinal, cross-sectional view of a simplified, schematic representation of the pump, showing respective polarities of the magnets and the pole pieces of the passive radial magnetic bearings, and the elements of the pump motor, including rotor magnets and a motor stator.
Figure 8:
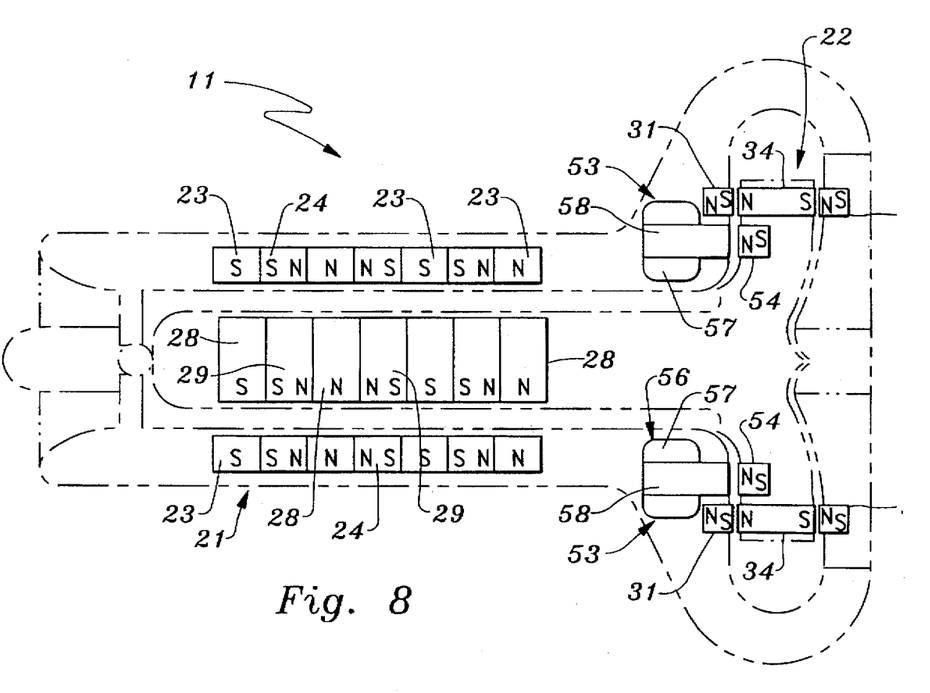

Accordingly, the forward magnetic bearing 21 includes a plurality of rings, comprising ferromagnetic pole pieces 23 and axially polarized permanent magnets 24. As shown most clearly in FIGS. 7 and 8, pole pieces 23 and magnets 24 are arranged in contingent, alternating fashion, and are located between outer sidewall 26 and inner sidewall 27 of inlet tube 13. The polarization of opposing magnets is the same, inducing an identical polarization into a respective pole piece therebetween. A combination of high strength adhesive and surrounding tube sidewalls, maintains the arrangement of magnets and pole pieces in contingent relation, despite strong magnet forces attempting to urge the rings apart.

Forward magnetic bearing 21 also includes a plurality of discs, comprising ferromagnetic pole pieces 28 and axially polarized permanent magnets 29. Pole pieces 28 and magnets 29 are also arranged in contingent, alternating fashion, so as to form a magnetic structure which mirrors the polarity and axial position of respective pieces and magnets of the surrounding rings. This magnetic structure is first assembled and secured together using high strength adhesive, and is then installed within the hollow volume of shaft or spindle 17. The magnetic polarizations and repulsive forces produced by the magnets and the pole pieces of forward magnetic bearing 21 are such that magnetic levitation of support shaft 18 results.

To provide additional radial restraint for rotor 17, rearward magnetic bearing 22 is also provided. Bearing 22 includes a first ring magnet 31 mounted on an outer wall of casing 14, and a second ring magnet 32 imbedded within a circular casing base 33. The bottom portion of casing 14 is attached and sealed to base 33, to form a fluid impervious enclosure for impeller 19 (see FIG. 7). Both magnets 31 and 32 are axially polarized, but each has a different polarization facing impeller 19. Bearing 22 also includes a plurality of rod magnets 34, transversely extending from an upper face portion 36 to a lower face portion 37 of impeller 19. Rod magnets 34 are arranged in spaced, circular fashion, adjacent an outer periphery 38 of impeller 19. The polarizations between the ends of magnets 34 and the adjacent surfaces of magnets 31 and 32 are respectively opposite, creating attractive, but equal and opposite magnetic forces acting on the impeller. In this manner, rearward magnetic bearing 22 acts to maintain the impeller end of rotor 17 in axial alignment.

It should also be noted that other configurations, locations, numbers, and polarization orientations may be used for the components forming rearward magnetic bearing 22. For example, magnets 34 may be arcuate segments, rather than rods. Also, the polarizations of the magnets 31, 32, and 34 may be arranged to effect respective repulsive forces, rather than the attractive forces specifically disclosed herein.

Although the drawings show magnets 32 and 34 as if portions thereof are directly immersed in blood, in actual practice, a thin-walled non-magnetic jacket or a plastic coating would be placed over these portions, to prevent contact between the magnets and the blood. Such contact, if it were allowed, would likely cause an undesirable chemical reaction, to the detriment of the blood. However, for clarity, the referenced jacket or coating, is not shown in the drawings.

To provide mechanical limitations on axial, translational excursions of the rotor, a first thrust bearing 39 and a second thrust bearing 41 are provided. First thrust bearing 39 includes a threaded plug 42, installed within casing base 33. Plug 42 is screw adjustable along the longitudinal axis of rotor 17, and includes a recessed bearing surface 43. Surface 43 is contoured to accommodate a corresponding bearing tip 44, in the lower face portion of impeller 19. It should be noted that the particular configuration of bearing 39 is not critical, and planar bearing surfaces may alternatively be used in this application.

Second thrust bearing 41 is secured within the blood entry end of inlet tube 13, and includes a spider 46, adjustment knob 47, and ball 48. Rotation of knob 47 will translate ball 48 along the longitudinal axis of rotor 17.

Alternative locations and constructions for second thrust bearing 41 are also contemplated. For example, an annular thrust bearing surface could be provided on the inner wall of casing 14, adjacent the upper face portion 36 of impeller 19. In this arrangement, portion 36 would slidably contact the annular thrust bearing surface. By eliminating spider 46 and the associated components of the upstream thrust bearing, the possibility of blood deposits forming on these structures would be eliminated.

It will be appreciated that thrust bearings 39 and 41 are effective not only to provide limit stops to axial movement of rotor 17, but also to adjust certain operational aspects of the pump. In the drawings, the upstream end of support shaft 18 is shown in contact with ball 48. However, this will not always be the case during the course of operating the pump. For example, it is desirable for the two thrust bearings to be adjusted so that the distance between them, is slightly greater than the overall length of the rotor. This will allow the rotor to "shuttle", back and forth between the axial constraints provided by the thrust bearings with each cardiac cycle of the user. Each such cycle will produce a pumping action, bringing fresh blood into the touchdown, or thrust bearing area.

The present invention does not use a journal bearing to restrain the rotor. Of necessity, a journal bearing radially encases at least a portion of the rotor's support shaft or spindle. It is within this thin, annular volume between the shaft and the bearing surface, where thrombosis can occur in prior art devices as a consequence of heat and excessive residence time within the bearing. The bi-stable operation of the pump and rotor of the present invention, continuously flushes the blood around each thrust bearing, avoiding thrombosis effects of prior art journal bearings.

There is also an important physical relationship which exists between the rotor and the magnetic bearings of the device disclosed herein. This relationship is established and maintained by proper axial placement of the adjustable thrust bearings. In operation of the pump, the pressure gradient produced by the rotating impeller imparts an upstream axial force on the rotor. This force needs to be substantially counterbalanced, to ensure that cardiac pulses will create sufficient pressure variances through the pump, to effect bi-stable operation. By adjusting the axial relationship of the pole pieces 23 and the magnets 24 with respect to the pole pieces 28 and magnets 29, a downstream axial force will be produced. Since the forces within forward magnetic bearing 21 are repulsive, the desired downstream loading or bias will be effected when the magnets and pole pieces within the shaft are translated slightly downstream from the magnets and pole pieces in the inlet tube (See, FIGS. 7 and 8). Thus, second thrust bearing 41 is effective to shift, or offset the rotor downstream a sufficient amount so the resultant, repulsive magnetic forces substantially counterbalance the hydrodynamic axial force produced by the rotating pump impeller.

Figure 6:
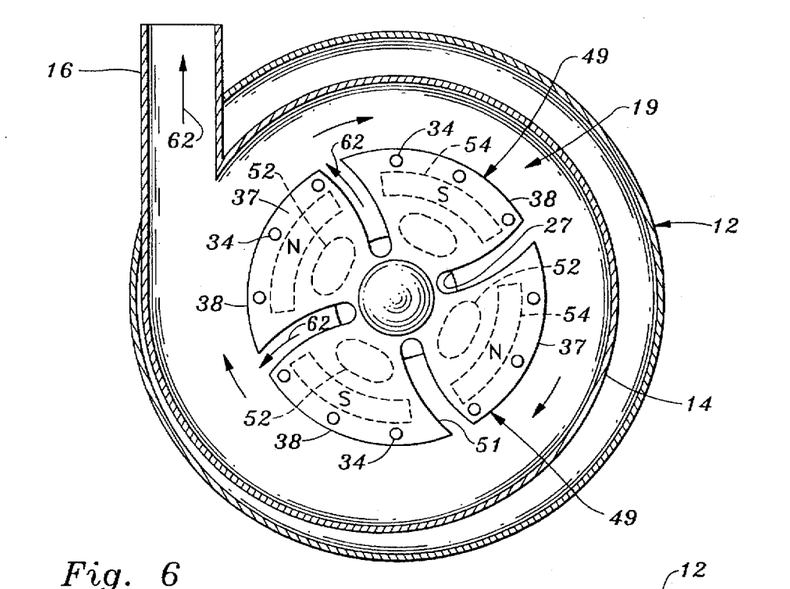
FIG. 6 is a transverse, cross-sectional view of the housing, impeller, and impeller chamber, taken along the line 6—6, shown in FIG. 1.

We can now turn to the special design considerations and operational characteristics of impeller 19. As will be noted particularly in FIG. 6, the impeller includes a plurality of large blade sectors 49. Owing to its relatively high viscosity and susceptibility to damage from heat and mechanical action, blood is a uniquely difficult liquid to pump.

It is generally preferable in a large centrifugal pump, to have a substantial number of thin, sharp impeller blades with relatively large voids or passages, between the blades, for the passage of low viscosity liquid. However, such a conventional design is not desirable, for a small centrifugal pump which has to pump a viscous liquid, such as blood.

When blood flows axially into the leading edges of impeller blades it tends to be damaged by the mechanical action and turbulence associated with the impeller blades. Thus, one of the design considerations of the present invention is to reduce such hemolysis, by minimizing the number of impeller blades.

To maintain efficiency in a small pump with so few blades, the effective working area of the blades needs to be increased. This was accomplished in the present design by modifying the size and configuration of conventional blades in two significant aspects. First, blade sectors 49 are made relatively wide or expansive through a rotational aspect (see FIG. 6). In other words, the outer periphery of each blade sector 49 assumes approximately 80 to 85 degrees of rotation. It should be noted that an alternative design contemplated herein includes only two blade sectors, each of which assumes approximately 175 degrees of rotation. In either case, the width of the impeller blade sectors of the present invention differ significantly from known prior art blades.

Figures 1, 2:
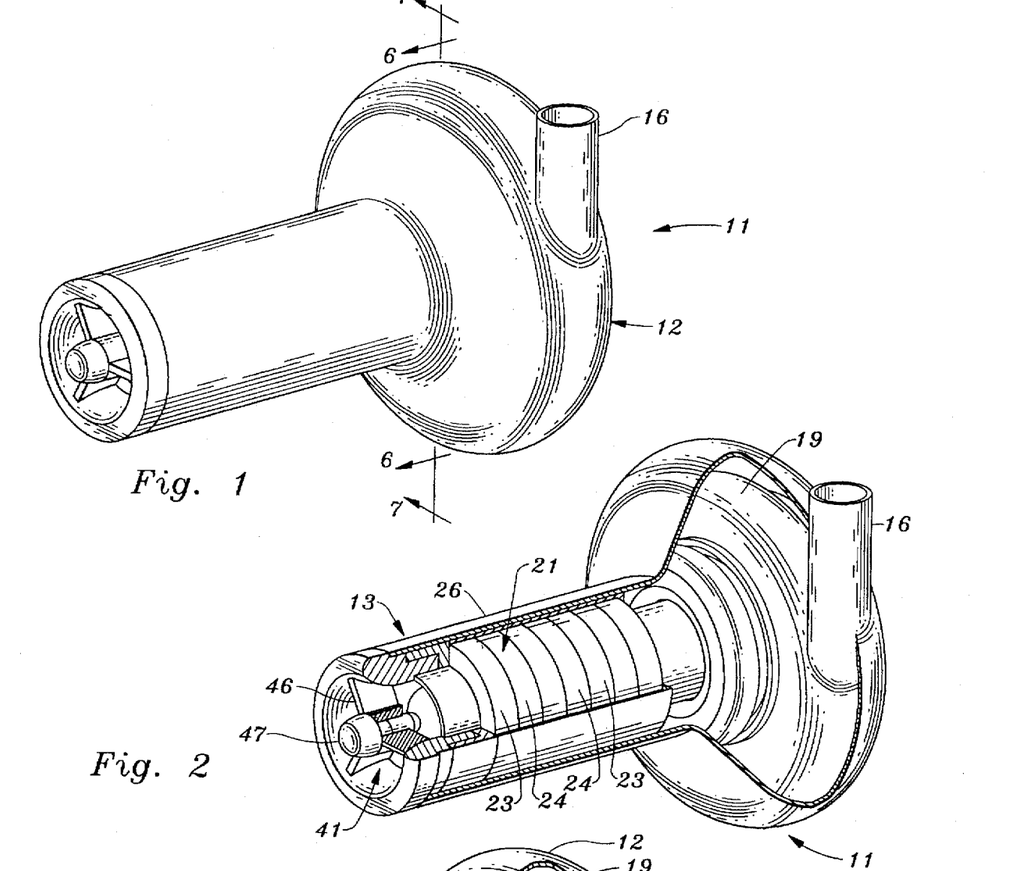
FIG. 1 is a left front perspective of the blood pump of the present invention.
FIG. 2 is a fragmentary, cross-sectional view of the pump of FIG. 1, showing a plurality of ring magnets comprising part of the magnetic bearing assembly.
Figure 3:
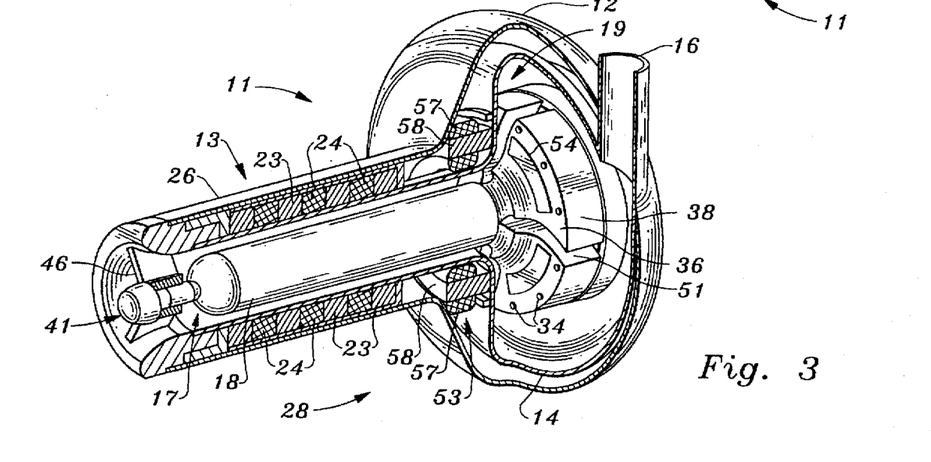
FIG. 3 is a fragmentary, cross-sectional view of the pump of FIG. 1, showing the shaft and an impeller.
Figure 4:
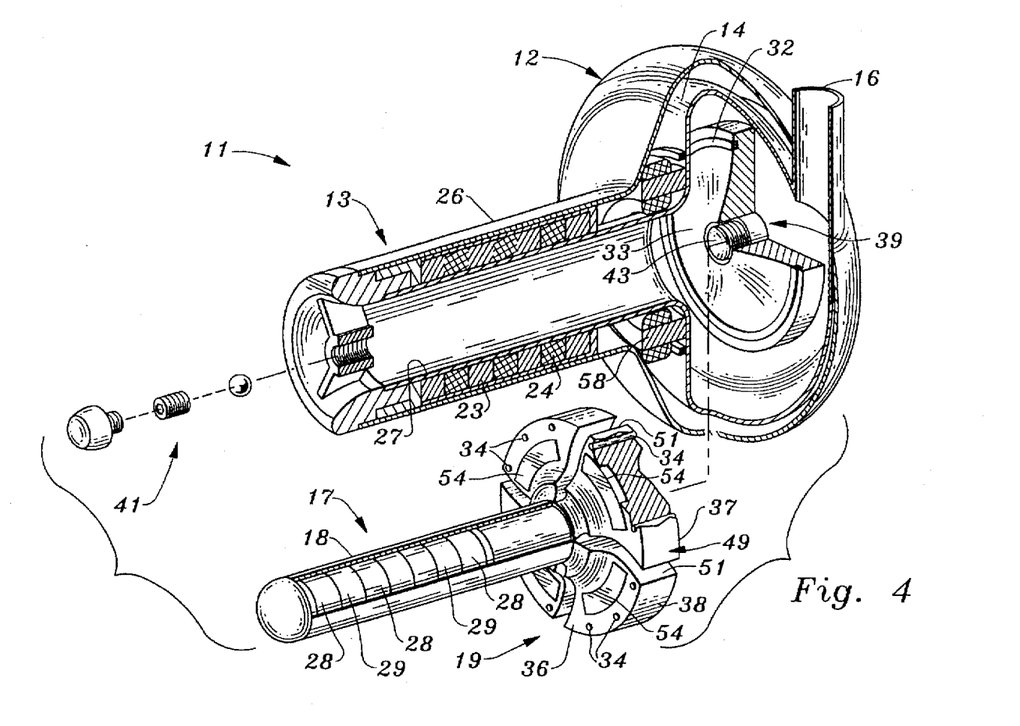
FIG. 4 is a view as in FIG. 1, but with the shaft and impeller shown removed from the housing.

The second modification pertains to the thickness or height of the blade sectors. As shown particularly in FIGS. 4 and 7, blade sectors 49 are relatively thick in an axial direction. As a consequence of these modifications, a narrow and deep impeller blood flow path or passageway 51 is defined between adjacent edges of blade sectors 49. By increasing the thickness of the blade sectors and narrowing the blood passageway, the ratio between the area of working surface of the blades and the volume of the passageway is increased. Also, the average distance of the liquid in the passageway from the working surface of the blades is decreased. Both of these beneficial results provide a small pump for blood which has few blades for damaging blood, yet maintains acceptable efficiency.

The size and configuration of the impeller blades also allows the structural integration of a number of features directly within the impeller 19. For example, the previously discussed rearward magnetic bearing 22 includes a plurality of rod magnets 34 of considerable length. Owing to the thickness of the blade sectors, these magnets are readily accommodated within the sectors. The sectors may also be provided with respective hollow chambers 52, to reduce the mass of the impeller and the gravity induced loads on the thrust bearings (see, FIG. 6).

Figure 5:
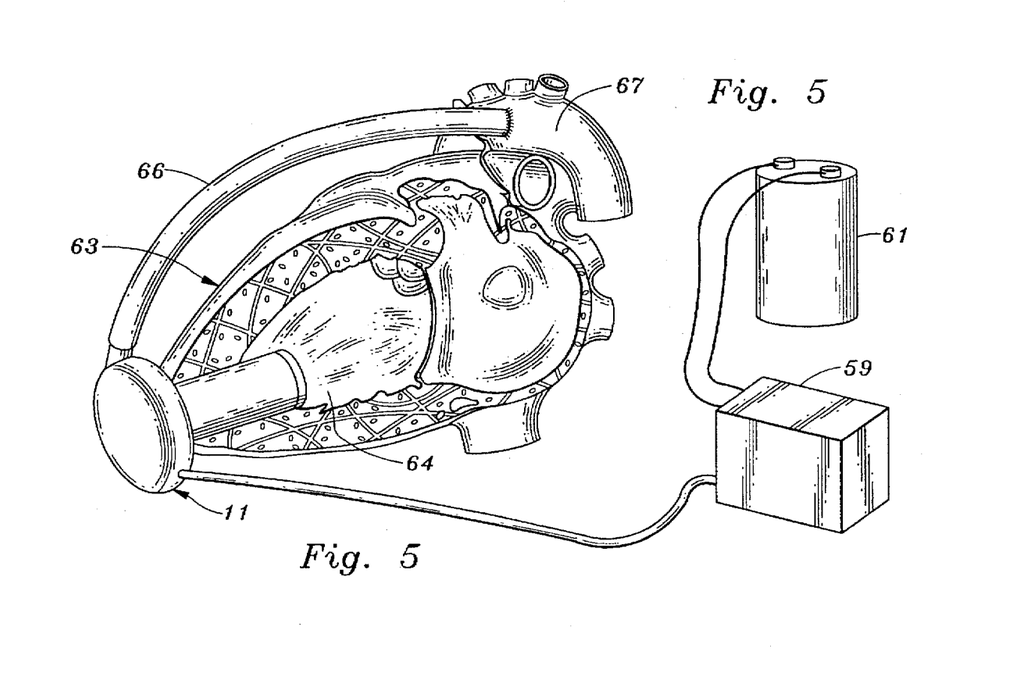
FIG. 5 is a simplified, fragmentary, representation of a human heart, showing the pump implanted within the left ventricle of the heart.

Lastly, a brushless rotor motor 53 includes arcuate magnetic segments 54, imbedded within the upper face portion 36 of blade sectors 49. As discussed above, the portions of segments 54 which would otherwise be in fluid communication with the pumped blood, are encased in a jacket or a coating (not shown) to prevent any chemical reaction between the blood and the magnetic segments. Making reference to FIGS. 6 and 8, segments 54 have alternating orientations in their polarities, and are directed toward an adjacent motor stator 56. Included within stator 56 are windings 57 and a circular pole piece 58, mounted on the outer surface of impeller casing 14. Windings 57 are interconnected by means of percutaneous wires to a controller 59 and a power supply 61, as shown in FIG. 5. It is contemplated that controller 59 and power supply 61 may be worn externally by the user, or alternatively, they may be completely implanted in the user.

Controller 59 may include circuitry as simple as a variable voltage or current control, manually adjusted or programmed to determine the running rate of pump. However, controller 59 may also have interactive and automatic capabilities. For example, controller 59 may be interconnected to sensors on various organs of the user, automatically and instantaneously to tailor operation of the pump to the user's physical activity and condition.

The windings 57 are energized by the electrical output of controller 59 to produce an electromagnetic field. This field is concentrated by pole piece 58, and is effective to drive magnets 54 and the rotor 17, in rotary fashion. The back EMF resulting from the magnets 54 passing by the windings is detected by the controller. The controller uses this back EMF voltage to continue generation of the electromagnetic field in synchronism with further rotation of the rotor. Brushless operation of the motor 53 is effected, then, by electromagnetic interaction between the stator and magnets imbedded within the pump's impeller blades.

Rotation of the rotor 17, including shaft 18 and impeller 19, causes blood to flow through inlet tube 13 in the direction of arrows 62. The blood continues its path from the upper edge of passage 51 to the interior of casing 14. Discharge tube 16 allows the blood to be expelled from the casing an into the user's cardiovascular system.

Anatomical placement of the pump 11 is shown in FIG. 5. The simplified representation of a human heart 63, includes a left ventricle 64 and an aorta 67. The inlet tube 16 serves as the inflow cannula and is placed into the apex of the left ventricle 64. An arterial vascular graft 66 is connected on one end to tube 16 and on the other end to the aorta 67 through an end to side anastomosis.

The centrifugal design of the pump allows a considerable amount of flexibility during implantation. Owing to the axial inflow and radial outflow of the pump, a 90 degree redirection of the blood is effected without the necessity of a flow-restrictive elbow fitting. Moreover, the pump can be rotated on its longitudinal axis to adjust the orientation of the discharge tube and minimize kinking and hydraulic losses in the vascular graft. Good anatomic compatibility is possible since the pump casing is compact and disc-shaped, fitting well between the apex of the heart and the adjacent diaphragm.

It will be appreciated, then, that I have provided an improved sealless blood pump including magnetic bearings and thrust bearing suspension to minimize thrombosis, and an impeller having a blood flow path therethrough which is calculated to minimize hemolysis.

What is claimed is:

1. A sealless blood pump, comprising:
   a. a pump housing, having an elongated inlet tube on one end and an impeller casing on the other end, said casing including a discharge tube;
   b. a rotor mounted for rotation within said housing, said rotor having an elongated shaft portion and an impeller attached to said shaft portion, said impeller being located within said impeller casing;
   c. radial magnetic bearings carried by said shaft potion, and radial magnetic bearings carried by said housing for maintaining said shaft portion of said rotor coaxially within said inlet tube of said housing, a primary flow channel for blood being provided by an annular volume between said shaft and said radial magnetic bearings carried by said housing;
   d. a thrust bearing for restraining said rotor from translating past a predetermined position along its axis;
   e. a motor rotor carried by said impeller; and
   f. a motor stator within said housing adjacent said impeller, for producing an electromagnetic field.

2. An apparatus as in claim 1 in which said radial magnet bearings bias said rotor axially against said thrust bearing.

3. A sealless blood pump comprising:
   a pump housing, having an elongated inlet tube on one end and an impeller casing on the other end, said casing including a discharge tube;
   a rotor mounted for rotation within said housing, said rotor having an elongated shaft portion and including an impeller attached to said shaft portion, said impeller being located within said impeller casing;
   radial magnetic bearings for maintaining said shaft portion of said rotor coaxially within said inlet tube of said housing, a blood flow path being provided by an annular volume between said shaft and said housing;
   a thrust bearing for restraining said rotor from translating past a predetermined position along its axis;
   a motor rotor on a surface of said impeller; and
   a motor stator within said housing adjacent said surface of said impeller, for producing an electromagnetic field;
   said thrust bearing restraining said rotor within two predetermined axial positions, between which said rotor may shuttle in response to a varying blood pressure across said inlet tube and said outlet tube.

4. An apparatus as in claim 1 in which said radial magnet bearings comprise a plurality of forward radial magnets, said forward radial magnets including a plurality of ring inlet magnets and a corresponding plurality of ring shaft magnets, in which like poles of corresponding inlet magnets and shaft magnets face each other.

5. An apparatus as in claim 4 in which said radial magnet bearings further comprise a plurality of rearward radial magnets, said rearward radial magnets including a plurality of casing magnets and a corresponding plurality of impeller magnets, in which said impeller is generally disc-like in configuration and said impeller magnets extend transversely through said impeller and are arranged in circular fashion around an outer periphery of said impeller, said casing magnets being located in either side of said impeller in proximity to respective impeller magnets, and in which opposite poles of corresponding casing magnets and impeller magnets face each other.

6. An apparatus as in claim 1 in which said motor rotor comprises a plurality of arcuate, planar, magnetic segments arranged in generally circular fashion on said surface of said impeller, said segments having outwardly facing poles of identical polarity.

7. An apparatus as in claim 6 in which said motor stator comprises a circular winding of electrically conductive wire, generally concentric with said shaft.

8. A sealless blood pump, comprising:
   a. a pump rotor, said rotor having an elongated shaft with an upstream end and a downstream end, said rotor further including an impeller attached to said downstream end of said shaft;
   b. a pump housing, said housing having an elongated inlet tube on one end, said shaft being enclosed by and concentric with said tube, said housing further including a casing on the other end surrounding said impeller, said casing having an outlet tube;
   c. radial magnetic bearings carried by said shaft portion and radial magnetic bearings carried by said housing for coaxially maintaining said shaft within said tubular inlet of said housing for rotation about a longitudinal axis, said radial magnetic bearings carried by said shaft and said radial magnetic bearings carried by said housing providing between them an annular volume defining a primary flow channel for blood;
   d. a first thrust bearing within said casing, said impeller having a bearing surface in contact with said first thrust bearing;
   e. a permanent magnet motor rotor carried by said impeller;
   f. an electromagnetic motor stator within said housing adjacent said impeller;
   g. a power supply having an electrical output in connection with said motor stator.

9. An apparatus as in claim 8 in which said impeller includes a plurality of blades with arcuate channels therebetween, said channels extending from an upstream portion of the blades to a downstream portion thereof, the downstream portion of each of said channels being oriented in a direction opposing a direction of impeller rotation.

10. An apparatus as in claim 8 in which said radial magnet bearings comprise a plurality of forward radial magnets, said forward radial magnets including a plurality of ring inlet magnets and a corresponding plurality of ring shaft magnets, in which like poles of corresponding inlet magnets and shaft magnets face each other.

11. An apparatus as in claim 10 in which said radial magnet bearing further comprise a plurality of rearward radial magnets, said rearward radial magnets including a plurality of casing magnets and a corresponding plurality of impeller magnets, in which said impeller is generally disc-like in configuration and said impeller magnets extend transversely through said impeller and are arranged in circular fashion around an outer periphery of said impeller, said casing magnets being located on either side of said impeller in proximity to a pole of a respective impeller magnets, and in which opposite poles of corresponding casing magnets and impeller magnets face each other.

12. An apparatus as in claim 8 further including a second thrust bearing within said inlet tube, said shaft having a bearing surface at said upstream end in contact with said second thrust bearing.

13. A sealless blood pump, comprising:
   a pump rotor, said rotor having an elongated shaft with an upstream end and a downstream end, said rotor further including an impeller attached to said downstream end of said shaft;
   a pump housing, said housing having an elongated inlet tube on one end, said shaft being enclosed by and concentric with said tube, said housing further including a casing on the other end surrounding said impeller, said casing having an outer tube;
   radial magnetic bearings for coaxially maintaining said shaft within said tubular inlet of said housing for rotation about a longitudinal axis, an annular volume between said shaft and said housing defining a blood flow path;
   a first thrust bearing within said casing, said impeller having a bearing surface in contact with said first thrust bearing;
   a permanent magnet motor rotor on a surface of said impeller;
   an electromagnetic motor stator within said housing adjacent said surface of said impeller;
   a power supply having an electrical output in connection with said motor stator;
   further including a second thrust bearing within said inlet tube, said shaft having a bearing surface at said upstream end in contact with said second thrust bearing;
   said first and second thrust bearings being spaced apart a distance slightly greater than the length of said rotor, wherein blood pressures between said inlet tube and said outlet tube vary to shuttle said rotor between said first and second thrust bearings.

14. An apparatus as in claim 8, in which said radial magnet bearings bias said rotor axially against said first thrust bearing.

15. An apparatus as in claim 8 in which said motor rotor includes a plurality of arcuate, planar, magnetic segments arranged in generally circular fashion on said surface of said impeller, said segments having outwardly facing poles of identical polarity.

16. An apparatus as in claim 8 in which said motor stator includes a circular winding of electrically conductive wire, generally concentric with said shaft.

17. A centrifugal blood pump having a rotor, an inlet tube and an impeller casing, said inlet tube including a bearing supporting the rotor for rotation about a longitudinal axis, comprising:
   a. said rotor being rotatable within the inlet tube, said rotor having an upstream end and a downstream end;
   b. a disc-shaped impeller having a central, upper face portion attached to said downstream end of said rotor and located within the casing, said impeller having a plurality of blade sectors, each of said sectors being separated from an adjacent sector by a channel extending continuously from said upper face portion to a lower face portion, each of said channels beginning with a leading edge, adjacent said shaft and ending with a trailing edge at an outer periphery of said impeller, said channel serving as a continuous fluid path through the impeller from said upper face portion to said lower face portion and functioning to increase the effective working area of the impeller; and
   c. a blood flow path on the outside of said rotor for bringing the blood to said upper face portion for passage through said channels.

18. A device as in claim 17 further including a rotor motor for rotating said shaft and said impeller in said direction of rotation.

19. A device as in claim 17 further including a rotor motor, said motor including: a plurality of permanent magnets on said upper face portion of said impeller; a motor stator adjacent said upper face portion of said impeller, said stator including an electrically conductive coil; and, a power supply providing electrical power to said stator, thereby imparting torque to said rotor in said direction of rotation.

20. A device as in claim 19 in which said permanent magnets include arcuate magnetic segments located on each of said sectors.

21. A sealless blood pump, comprising:

a pump housing, having an inlet tube on one end and an impeller casing on the other end, said casing including an outlet;

a rotor mounted for rotation within said housing, said rotor having an elongated shaft portion and including an impeller attached to said shaft portion, said impeller being located within said impeller casing;

radial magnetic bearings carried by said shaft portion, and radial magnetic bearings carried by said housing for maintaining said shaft portion of said rotor within said inlet tube of said housing, a primary flow channel for blood being provided by an annular volume between said shaft and said radial magnetic bearings carried by said housing; and thrust bearings for restraining said rotor from translating past a predetermined position along its axis, said thrust bearings restraining said rotor within two predetermined axial positions, between which said rotor may shuttle in response to a varying blood pressure across said inlet tube and said outlet.

22. A sealless blood pump, comprising:

a pump housing, having an inlet tube on one end and an impeller casing on the other end, said casing including an outlet;

a rotor mounted for rotation within said housing, said rotor having an elongated shaft portion and an impeller attached to said shaft portion, said impeller being located within said impeller casing;

radial magnetic bearings for maintaining said shaft portion of said rotor within said inlet tube of said housing, a blood flow path being provided by an annular volume between said shaft and said housing;

thrust bearings for restraining said rotor from translating past a predetermined position along its axis, said thrust bearings restraining said rotor within two predetermined axial positions, between which said rotor may shuttle in response to a varying blood pressure across said inlet tube and said outlet;

said thrust bearings being located at opposed ends of said rotor with the distance between said thrust bearings being greater than the overall length of said rotor.

23. A sealless blood pump as defined by claim 22, in which at least one of said thrust bearings is adjustable thereby enabling the distance between thrust bearings to be adjusted so that the distance between the thrust bearings is slightly greater than the overall length of the rotor.

24. A sealless centrifugal blood pump having an inlet tube and an impeller casing, said inlet tube including a bearing for supporting a rotor for rotation about a longitudinal axis, comprising:

a rotor, said rotor comprising a rotatable, elongated support shaft within the inlet tube, said shaft having an upstream end and a downstream end;

a disc-shaped impeller having a central, upper face portion attached to said downstream end of said shaft and located within the casing, said impeller having a plurality of blade sectors, each of said sectors being separated from an adjacent sector by a channel extending from said upper face portion to a lower face portion;

said channels serving as a fluid path through the impeller and functioning to increase the effective working area of the impeller; and a plurality of permanent magnets unitary with and located within said blade sectors.

25. A sealless centrifugal blood pump as defined by claim 24, in which said impeller is thick in the axial direction and said permanent magnets comprise magnets which extend substantially through said impeller in the axial direction.

26. A sealless centrifugal blood pap having an inlet tube and an impeller casing, said inlet tube including a bearing for supporting a rotor for rotation about a longitudinal axis, comprising:

a rotor, said rotor comprising a rotatable, elongated support shaft within the inlet tube, said shaft having an upstream end and a downstream end;

a disc-shaped impeller having a central, upper face portion attached to said downstream end of said shaft and located within the casing, said impeller being thick in the axial direction and having a plurality of blade sectors, each of said sectors being separated from an adjacent sector by a channel extending from said upper face portion to a lower face portion;

said channels serving as a fluid path through the impeller and functioning to increase the effective working area of the impeller; and said impeller blade sectors defining sealed, individual hollow chambers to reduce the density of the impeller.

27. A sealless centrifugal blood pump as defined by claim 26, including a plurality of permanent magnets carried by said impeller, and in which said impeller is thick in the axial direction and said permanent magnets comprise magnets which extend substantially through said impeller in the axial direction.

28. A sealless blood pump, comprising:

a pump housing, having an inlet tube on one end and an impeller casing on the other end, said casing including an outlet;

a rotor mounted for rotation within said housing, said rotor having an elongated shaft portion and an impeller attached to said shaft portion, said impeller being located within said impeller casing;

radial magnetic bearings carried by said shaft portion, and radial magnetic bearings carried by said housing for maintaining said shaft portion of said rotor within said inlet tube of said housing, a primary flow channel for blood being provided by an annular volume between said shaft and said radial magnetic bearings carried by said housing; and a rotor motor, said motor including a plurality of permanent magnets carried by said impeller, a motor stator including an electrically conductive coil, said motor stator having a ring-shaped configuration and surrounding said rotor.

29. A sealless blood pump as defined by claim 28, in which said ring-shaped motor stator is in axial alignment with said permanent magnets.

30. A sealless blood pump as defined by claim 28, in which said ring-shaped stator comprises a circular pole piece surrounded by windings.

31. A sealless blood pump as defined by claim 28, in which said magnets carried by the impeller comprise arcuate magnetic segments.

32. A sealless blood pump, comprising:
    a pump housing, having an inlet tube on one end and an impeller casing on the other end, said casing including an outlet;
    a rotor mounted for rotation within said housing, said rotor having an elongated shaft portion with a transverse dimension smaller than an inner dimension of said inlet tube, said rotor further including an impeller attached to said shaft portion, said impeller being located within said impeller casing;
    radial magnetic bearings for maintaining said shaft portion of said rotor within said inlet tube of said housing, a blood flow path being provided by an annular volume between said shaft and said inner diameter; and
    a thrust bearing for restraining said rotor from translating past a predetermined position along its axis, said thrust bearing being located outside of the axis of rotation of said rotor.

33. A sealless blood pump as defined in claim 32, in which said thrust bearing outside of said axis of rotation of said rotor comprises an annular thrust bearing surface on said casing, adjacent a face of said impeller.

34. A sealless blood pump as defined by claim 33, in which said casing has an inner wall and an outer wall, said impeller has an upper face and a lower face, and said annular thrust bearing surface is positioned on said inner wall of said casing, adjacent said upper face of said impeller.

35. A sealless blood pump as defined by claim 32, including a second thrust bearing operating with said first mentioned thrust bearing for restraining said rotor to predetermined axial positions, between which said rotor may shuffle in response to a varying blood pressure across said inlet tube and said outlet.

36. A sealless blood pump as defined in claim 35, in which at least one of said thrust bearings is adjustable thereby enabling the distance between thrust bearings to be adjusted.

37. A sealless blood pump, comprising:
    a pump housing;
    a rotor mounted for rotation within said housing;
    radial magnetic bearings for maintaining said rotor within said housing; and
    thrust bearings for restraining said rotor from translating past a predetermined position along its axis, said thrust bearings restraining said rotor within two axial positions between which said rotor may shuttle in response to a varying blood pressure.

38. A sealless blood pump as defined by claim 35, in which said thrust bearings are located at opposed ends of said rotor with a distance between said thrust bearings being greater than the overall length of said rotor, at least one of said thrust bearings being adjustable thereby enabling the distance between thrust bearings to be adjusted.

39. A sealless blood pump, comprising:
    a pump housing, having an inlet tube on one end and an impeller casing on the other end, said casing including an outlet;
    a rotor mounted for rotation within said housing, said rotor having an elongated shaft portion and including an impeller attached to said shaft portion, said impeller being located within said impeller casing;
    radial magnetic bearings carried by said shaft portion, and radial magnetic bearings carried by said housing for maintaining said shaft portion of said rotor within said inlet tube of said housing, a primary flow channel for blood being provided by an annular volume between said shaft and said radial magnetic bearings carried by said housing; and
    a thrust bearing for restraining said rotor from translating past a predetermined position along its axis, said thrust bearing being located outside of the axis of rotation of said rotor.

40. A sealless blood pomp as defined in claim 39, in which said thrust bearing outside of said axis of rotation of said rotor comprises an annular thrust bearing surface on said casing, adjacent a face of said impeller.

41. A sealless blood pump as defined by claim 40, in which said casing has an inner wall and an outer wall, said impeller has an upper face and a lower face, and said annular thrust bearing surface is positioned on said inner wall of said casing, adjacent said upper face of said impeller.

42. A sealless blood pump as defined by claim 39, including a second thrust bearing operating with said first mentioned thrust bearing for restraining said rotor to predetermined axial positions, between which said rotor may shuffle in response to a varying blood pressure across said inlet tube and said outlet.

43. A sealless blood pump as defined in claim 42, in which at least one of said thrust bearings is adjustable thereby enabling the distance between thrust bearings to be adjusted.

44. A sealless blood pump, comprising:
    a pump housing, having an inlet tube on one end and an impeller casing on the other end, said casing including an outlet;
    a rotor mounted for rotation within said housing, said rotor having an elongated shaft portion and an impeller attached to said shaft portion, said impeller being located within said impeller casing;
    radial magnetic bearings carried by said shaft portion, and radial magnetic bearings carried by said housing for maintaining said shaft portion of said rotor within said inlet tube of said housing, a primary flow channel for blood being provided by an annular volume between said shaft and said radial magnetic bearings carried by said housing; and
    a rotor motor, said motor including a plurality of permanent magnets located within said impeller and extending axially; a motor stator including an electrically conductive coil, said motor stator having a ring-shaped configuration and located within said housing.

* * * * *